(12) United States Patent
Wagner

(10) Patent No.: US 8,348,896 B2
(45) Date of Patent: Jan. 8, 2013

(54) PATENCY CHECK WITH PRESSURE MONITORING

(75) Inventor: Gary S. Wagner, Independence, KY (US)

(73) Assignee: Mallinckrodt LLC, Hazelwood, MO (US)

( * ) Notice: Subject to any disclaimer, the term of this patent is extended or adjusted under 35 U.S.C. 154(b) by 119 days.

(21) Appl. No.: 12/742,938

(22) PCT Filed: Nov. 19, 2008

(86) PCT No.: PCT/US2008/012920
§ 371 (c)(1),
(2), (4) Date: May 14, 2010

(87) PCT Pub. No.: WO2009/067212
PCT Pub. Date: May 28, 2009

(65) Prior Publication Data
US 2010/0249704 A1    Sep. 30, 2010

Related U.S. Application Data

(60) Provisional application No. 60/988,888, filed on Nov. 19, 2007.

(51) Int. Cl.
*A61M 1/00* (2006.01)
(52) U.S. Cl. ........................................ 604/118
(58) Field of Classification Search ........... 604/118, 604/121, 151, 65–71
See application file for complete search history.

(56) References Cited

U.S. PATENT DOCUMENTS

| | | | | |
|---|---|---|---|---|
| 4,534,756 A * | 8/1985 | Nelson | ............. | 604/505 |
| 4,854,324 A * | 8/1989 | Hirschman et al. | ............. | 600/432 |
| 4,959,050 A * | 9/1990 | Bobo, Jr. | ............. | 604/505 |
| 5,840,026 A * | 11/1998 | Uber et al. | ............. | 600/431 |
| 5,868,710 A * | 2/1999 | Battiato et al. | ............. | 604/123 |
| 5,925,022 A * | 7/1999 | Battiato et al. | ............. | 604/208 |
| 6,004,292 A * | 12/1999 | Battiato et al. | ............. | 604/123 |
| 6,159,183 A * | 12/2000 | Neer et al. | ............. | 604/189 |
| 6,470,889 B1 * | 10/2002 | Bae et al. | ............. | 604/28 |
| 6,635,030 B1 * | 10/2003 | Bae et al. | ............. | 604/131 |
| 7,044,933 B2 * | 5/2006 | VanDiver et al. | ............. | 604/151 |
| 7,753,885 B2 * | 7/2010 | Duchon et al. | ............. | 604/151 |
| 7,854,726 B2 * | 12/2010 | Fago et al. | ............. | 604/187 |
| 2002/0007116 A1 | 1/2002 | Zatezalo et al. | | |
| 2003/0095150 A1 | 5/2003 | Trevino et al. | | |
| 2004/0133165 A1 * | 7/2004 | Duchon et al. | ............. | 604/151 |
| 2005/0203389 A1 | 9/2005 | Williams | | |
| 2006/0079768 A1 * | 4/2006 | Small et al. | ............. | 600/432 |
| 2006/0079842 A1 * | 4/2006 | Small et al. | ............. | 604/151 |
| 2006/0079843 A1 * | 4/2006 | Brooks et al. | ............. | 604/151 |
| 2006/0122555 A1 * | 6/2006 | Hochman | ............. | 604/67 |
| 2007/0083152 A1 * | 4/2007 | Williams et al. | ............. | 604/65 |
| 2007/0100282 A1 * | 5/2007 | Small et al. | ............. | 604/151 |
| 2007/0106153 A1 * | 5/2007 | Neer et al. | ............. | 600/432 |
| 2008/0108943 A1 * | 5/2008 | Wagner | ............. | 604/151 |
| 2010/0249704 A1 * | 9/2010 | Wagner | ............. | 604/121 |
| 2010/0293496 A1 * | 11/2010 | Lafferty et al. | ............. | 715/772 |

* cited by examiner

*Primary Examiner* — Nicholas Lucchesi
*Assistant Examiner* — Diva K Chander
(74) *Attorney, Agent, or Firm* — Marsh, Fischmann & Breyfogle LLP

(57) ABSTRACT

A patency check protocol (150) for evaluating a patency check injection (156) is disclosed. The protocol (150) incorporates a pressure standard (152) (e.g., a pressure threshold; a target pressure curve). A pressure associated with the patency check injection is monitored (160) and compared against this pressure standard (164). If a first condition is identified (166) (e.g., if the pressure threshold is reached; if the monitored pressure deviates from the target pressure curve by more than a certain predetermined amount), one or more actions may be undertaken (168) (e.g., one or more notifications or alerts may be issued; the flow rate may be reduced for the patency check injection; the patency check injection may be suspended/terminated).

22 Claims, 8 Drawing Sheets

PATENCY CHECK WITH PRESSURE MONITORING

CROSS-REFERENCE TO RELATED APPLICATIONS

This patent application claims priority under 35 U.S.C. §119(e) to pending U.S. Provisional Patent Application Ser. No. 60/988,888, that is entitled "PATENCY CHECK WITH PRESSURE MONITORING," and that was filed on Nov. 19, 2007.

FIELD OF THE INVENTION

The present invention generally relates to the field of injecting fluid into a patient and, more particularly, to evaluating a flowpath extending to the patient prior to executing an injection protocol.

BACKGROUND

Various medical procedures require that one or more fluids be injected into the patient. Medical imaging procedures oftentimes involve the injection of contrast media into the patient, possibly along with saline or other fluids. Other medical procedures involve injecting one or more fluids into a patient for therapeutic purposes.

Consider the case where both contrast media and saline are to be injected into a patient in accordance with a certain injection protocol. This injection protocol may entail injecting a certain volume of contrast media at a certain flow rate into the patient, followed by injecting a certain volume of saline at a certain flow rate into the patient, followed by injecting a certain volume of contrast media at a certain flow rate into the patient. In the case where a power injector is being used to execute an injection protocol, it is common to monitor a pressure associated with both a contrast media injection and a subsequent saline injection. It is also common for a pressure threshold to be input to the power injector and to take one or more actions if this pressure threshold is reached or exceeded during both a contrast media injection and a saline injection phase of an injection protocol.

Fluid being injected into a patient may be unintentionally directed into patient tissue versus a vein. This is generally referred to as extravasation, and may be the result of a technologist missing the patient's vein entirely when inserting a catheter, by the technologist piercing through the vein when inserting the catheter, or by the vein rupturing during a fluid injection. A patency test or check may be undertaken prior to initiating an injection protocol. This patency check may entail manually injecting saline into the patient through the flowpath that is to be used for the actual injection procedure. If there is a blockage in the flowpath or if the flowpath terminates in patient tissue versus within the patient's vein, the technologist should feel "back-pressure" when pushing on the syringe plunger. The technologist may also touch the patient's skin in proximity to the injection site during the patency check to determine if fluid is entering the patient's vein—there may be a bulging of the patient's skin at the injection site if fluid is being directed into patient tissue versus the patient's vein.

Power injectors may be used to execute an injection protocol. A power injector generally includes what is commonly referred to as a powerhead. One or more syringes may be mounted to the powerhead in various manners (e.g., detachably; rear-loading; front-loading). Each syringe typically includes what may be characterized as a syringe plunger, piston, or the like. Each such syringe plunger is appropriately interconnected with an appropriate syringe driver that is incorporated into the powerhead, such that operation of the syringe driver axially advances the associated syringe plunger. One typical syringe driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

At least certain power injectors include a patency check or test feature that is software-based. A small quantity of saline (e.g., about 10 milliliters) may be injected at the maximum flow rate that is anticipated to be used for the actual injection protocol. This patency check injection is done prior to executing the injection protocol. The back-pressure that develops during the patency check injection may be displayed. However, this pressure-monitoring functionality is not integrated with the patency check functionality. That is, pressure information is not provided to the logic that controls the patency check injection.

SUMMARY

A first aspect of the present invention is embodied by a power injector. This power injector includes a powerhead, a syringe plunger drive assembly, and patency check logic. The patency check logic includes a pressure standard and is configured to execute a patency check injection.

Various refinements exist of the features noted in relation to the first aspect of the present invention. Further features may also be incorporated in the first aspect of the present invention as well. These refinements and additional features may exist individually or in any combination. The power injector may be of any appropriate size, shape, configuration, and/or type. The such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Such a power injector may be used for any appropriate application where the delivery of one or more fluids is desired, including without limitation any appropriate medical application (e.g., computed tomography or CT imaging; magnetic resonance imaging or MRI; SPECT imaging; PET imaging; X-ray imaging; angiographic imaging; optical imaging; ultrasound imaging). The power injector may be used in conjunction with any component or combination of components, such as an appropriate imaging system (e.g., a CT scanner). For instance, information could be conveyed between the power injector and one or more other components (e.g., scan delay information, injection start signal, injection rate).

Any appropriate number of syringes may be integrated with the power injector in any appropriate manner (e.g., detachably; front-loaded; rear-loaded; side-loaded), any appropriate fluid may be discharged from a given syringe of the power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit, where this conduit is fluidly interconnected with the syringe in any appropriate manner and directs fluid to a desired location (e.g., into a patient). In one embodiment, each syringe includes a syringe barrel and a plunger that is disposed within and movable relative to the syringe barrel. This plunger may interface with the power injectors syringe plunger drive assembly such that the syringe plunger drive assembly is able to advance the plunger in at least one direction, and possibly in two different, opposite directions.

The power injector may include pressure monitoring logic. This pressure monitoring logic may be utilized to monitor pressure associated with the operation of the power injector, including without limitation pressure in a flowpath extending from the power injector to a patient during a patency check injection, during execution of an injection protocol, or both. Any appropriate number and/or type of sensors may be utilized to monitor pressure. An output from the pressure monitoring logic may be provided to the patency check logic, for instance for comparison with the pressure standard. In one embodiment, a back-pressure in a flowpath extending from the power injector to a patient is monitored at least during a patency check injection.

The patency check logic may be of any appropriate form and/or type, for instance implemented by software, hardware, firmware, and any combination thereof. In one embodiment, the functionality provided by the patency check logic is executed using one or more processors of any appropriate size, shape, configuration, and/or type. In one embodiment, the functionality provided by the patency check logic is executed using one or more computers.

The pressure standard utilized by the patency check logic may be in the form of a pressure threshold for a patency check injection. This pressure standard may also be in the form of a target pressure curve (e.g., a "normal" change in pressure over time for a patency check injection). The patency check logic may be configured to compare a monitored pressure during a patency check injection with the pressure standard to identify any existence of a first condition. The current pressure reading may be updated on any appropriate basis (e.g., every "x" milliseconds). In one embodiment, the noted first condition is when a monitored pressure during a patency check injection reaches or exceeds a pressure threshold. In another embodiment, the noted first condition is when a monitored pressure during a patency check injection deviates from a target pressure curve by more that a certain amount. In any case, at least one data entry device may be operatively interconnected with the patency check logic such that the pressure standard may be input by an operator or the like. Any appropriate data entry device may be utilized, such as a touch screen display, a soft key display, a keyboard, a mouse, a touch pad, a track ball, or the like.

The power injector may utilize at least one display (e.g., on the powerhead, on a remote console). The patency check logic may be operatively interconnected with this display and configured to present on this display a representation of a monitored pressure value from a patency check injection. This representation of a monitored pressure value may be in any appropriate form, for instance a numeric representation of a pressure value, a graphical representation of a pressure value, or both. The patency check logic may be configured to provide the representation of a monitored pressure on any appropriate basis, such as in real-time during the patency check injection, only at the completion of the patency check injection, or both in real-time during the patency check injection and at the completion of the patency check injection.

Any appropriate action or combination of actions may be initiated in response to the patency check logic identifying a first condition (e.g., utilizing the pressure standard). The patency check logic may be configured to terminate or at least suspend a patency check injection if a first condition is identified by the patency check logic. The patency check logic may be configured to reduce a flow rate being utilized for the patency check injection if the patency check logic identifies a first condition. The patency check logic may be configured to provide at least one notification when the patency check logic identifies a first condition. Each notification may be of any appropriate form and may be presented any appropriate location or combination of locations. Representative notification forms include without limitation a textual message, a numeric message, an alphanumeric message, at least one optical or visual alarm (e.g., a "flashing" message), at least one audible alarm, or any combination thereof.

Any appropriate relationship or combination of relationships may be utilized between a patency check injection and a subsequent execution of an injection protocol. In one embodiment, the patency check logic is configured to display a message upon completion of a patency check injection, and the power injector may be configured so as to require a "clearing" of this message before an injection protocol may be subsequently executed. User input may be required after executing a patency check injection and prior to executing an injection protocol. The power injector may include injection protocol logic for purposes of executing/controlling an injection protocol. This injection protocol logic may be operatively interconnected with or operatively interface the patency check logic. In one embodiment, the injection protocol logic utilizes a comparator. One input to this comparator may be a pressure that was identified during a patency check injection (e.g., a maximum pressure encountered during the patency check injection, but where a first condition was not determined to exist between this maximum pressure and the pressure standard; a pressure value based at least in part on the noted maximum pressure), and a second input to this comparator may be a monitored pressure during a subsequent execution of an injection protocol. In one embodiment, a patency check pressure threshold may be input in any appropriate manner to the patency check logic, and an injection protocol pressure threshold may be input to the injection protocol logic in any appropriate manner. Each of the patency check and injection protocol pressure thresholds may be of any appropriate value, including being of the same magnitude or of different magnitudes.

A second aspect of the present invention is embodied by a method for executing a first medical procedure. A patient may be fluidly interconnected with a power injector. A first fluid may be injected into the patient through operation of the power injector, and this first fluid is the initial fluid that is injected into the patient by the power injector for the first medical procedure. The injection of the first fluid into the patient is monitored, and an output from this monitoring of the injection of the first fluid is compared with a first standard (e.g., using power injector control logic). A second fluid is injected into the patient using the power injector at some point in time after the first fluid has been injected.

Various refinements exist of the features noted in relation to the second aspect of the present invention. Further features may also be incorporated in the second aspect of the present invention as well. These refinements and additional features may exist individually or in any combination. The various features noted above in relation to the power injector of the first aspect may be utilized by the second aspect, individually or in any appropriate combination. In one embodiment, the power injector includes first and second syringes that are each mounted on the powerhead. Fluidly interconnecting the patient with the power injector may include fluidly interconnecting the patient with each of the first and second syringes. In one embodiment, the first syringe includes contrast media and the second syringe includes saline. The first and second syringes may provide fluid to a common patient injection site (e.g., through "Y" tubing or the like) or otherwise.

The injection of a first fluid may be a patency check injection. The first fluid may be of any appropriate type, such as saline. In one embodiment, the amount of the first fluid that is injected into the patient is no more than about 20 milliliters. In one embodiment, a flow rate that is used for injecting the first fluid is the maximum injected flow rate that is intended to be utilized for the first medical procedure. However, any appropriate flow rate may be used to inject the first fluid into the patient.

After the second fluid has been injected into the patient using the power injector, a third fluid may be injected into the patient using the power injector. This third fluid may be of any appropriate type, such as being of the same type as the first fluid. In one embodiment, the first and third fluids are discharged from a common syringe on the power injector. In this case, one distinction between the first and third fluids would be that the first fluid is the initial fluid injected into the patient by the power injector, whereas the third fluid is a subsequent-in-time injected fluid.

The second aspect may include monitoring an injection site for extravasation. The term "extravasation" as used herein means the introduction of fluid into patient tissue versus a vein. The injection of the first fluid, the monitoring of this first fluid injection, and the comparison of the monitoring output with the first standard may be characterized as collectively providing this extravasation monitoring function. The injection of the first fluid, the monitoring of this first fluid injection, and the comparison of the monitoring output with the first standard may be characterized as collectively providing a flowpath blockage check function, where this flowpath extends from the power injection to the patient.

The monitoring of the first fluid injection may be in the form of monitoring a pressure associated with this injection (e.g., a pressure in at least part of a flowpath extending from a power injector to the patient). The monitoring of the first fluid injection may be in the form of monitoring a back-pressure associated with this injection (e.g., a back-pressure pressure in at least part of a flowpath extending from a power injector to the patient). In one embodiment, the first standard is in the form of a pressure threshold or limit (e.g., a certain value). In another embodiment, the first standard is the form of a target pressure curve, for what may be considered to be a "normal" change in pressure over time for the patency check injection.

A first pressure threshold for the first fluid injection may be set, as may be a second pressure threshold for the second fluid injection. The setting of these two pressure thresholds may be independently executed. The values of the first and second pressure thresholds may be the same or different. Each of the first and second pressure thresholds may be of any appropriate value.

The comparison of the monitoring output with the first standard may be executed by power injector control logic (e.g., in the form of software, hardware, firmware, and any combination thereof), by one or more processors, by one or more computers, and any combination thereof. In one embodiment, the comparison of the monitoring output from the first fluid injection with the first standard includes determining if a first relationship exists between the monitoring output and the first standard. For instance, the comparison may be in the form of determining if the value of the monitoring output has met or exceeded a pressure threshold associated with the first fluid injection. The comparison may also be in the form of determining if the monitoring output has deviated by more than a certain predetermined amount from a target pressure curve.

At least one notification may be issued in response to the comparison being made of the first standard with the monitoring output from the first fluid injection. This notification may be issued when the comparison identifies the existence of a first condition. This first condition may be equated with at least a potential blockage associated with a flowpath between the power injector and the patient, at least a certain flow rate reduction associated with the first fluid injection, with the monitoring output being different from the first standard by more than a predetermined amount, with the monitoring output reaching or exceeding a pressure threshold, with the monitoring output deviating from a target pressure curve by more than a predetermined amount, or any combination thereof.

At least one action may be undertaken in response to the comparison of the monitoring output with the first standard, for instance if a first condition has been identified in relation to the first fluid injection. Representative actions include issuing at least one notification, issuing at least one alert, posting or displaying at least one message, reducing a flow rate associated with the first fluid injection, terminating the first fluid injection, numerically displaying a value that is representative of the monitoring output, graphically displaying a value that is representative of the monitoring output, and requiring a user to provide at least a certain type of input before the second fluid injection may be initiated.

DETAILED DESCRIPTION

Figure 1:
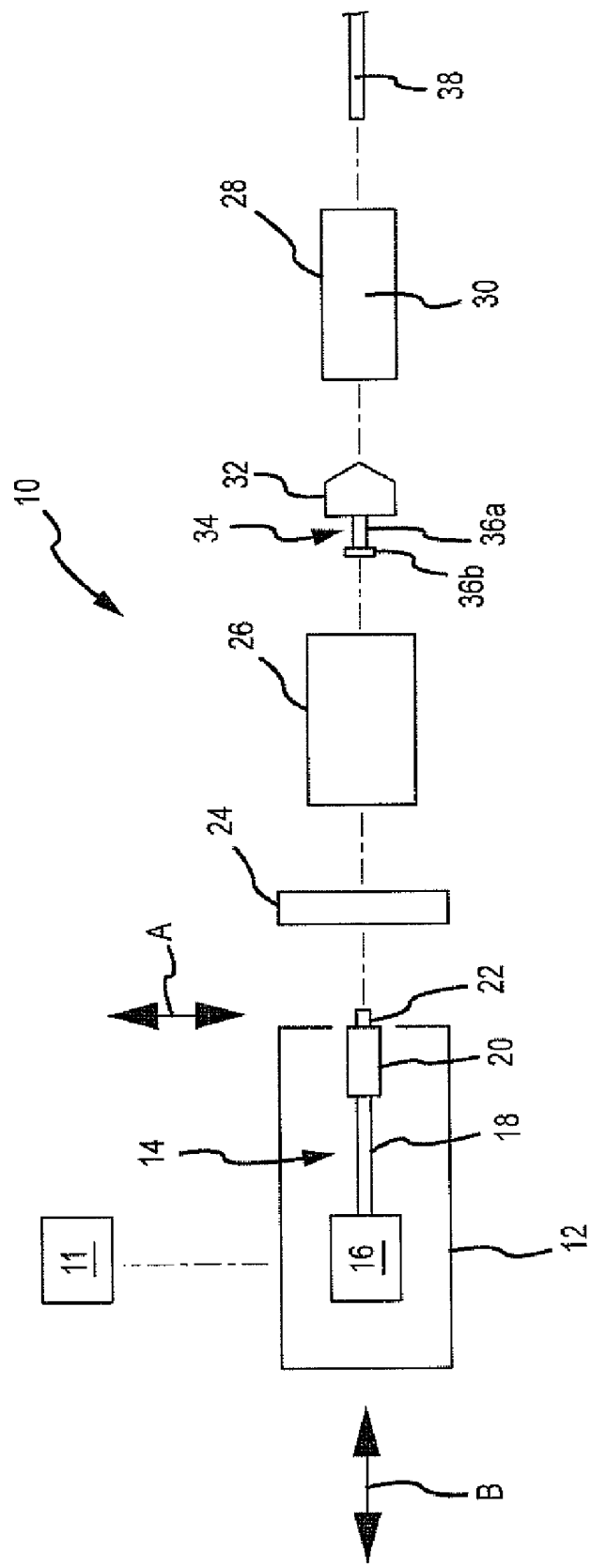
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically installed on the powerhead 12, followed by disposing the syringe 28 within the pressure jacket 26. The same pressure jacket 26 will typically remain installed on the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly 14 that interacts (e.g., interfaces) with the syringe 28 to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interfacing or interacting with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interface or interact with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 may interact with each syringe plunger 32 of the power injector 10 in any appropriate manner (e.g., by mechanical contact; by an appropriate coupling (mechanical or otherwise)) so as to be able to move or advance the syringe plunger 32 in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be required. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply "push on" the syringe plunger coupler 34 or on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
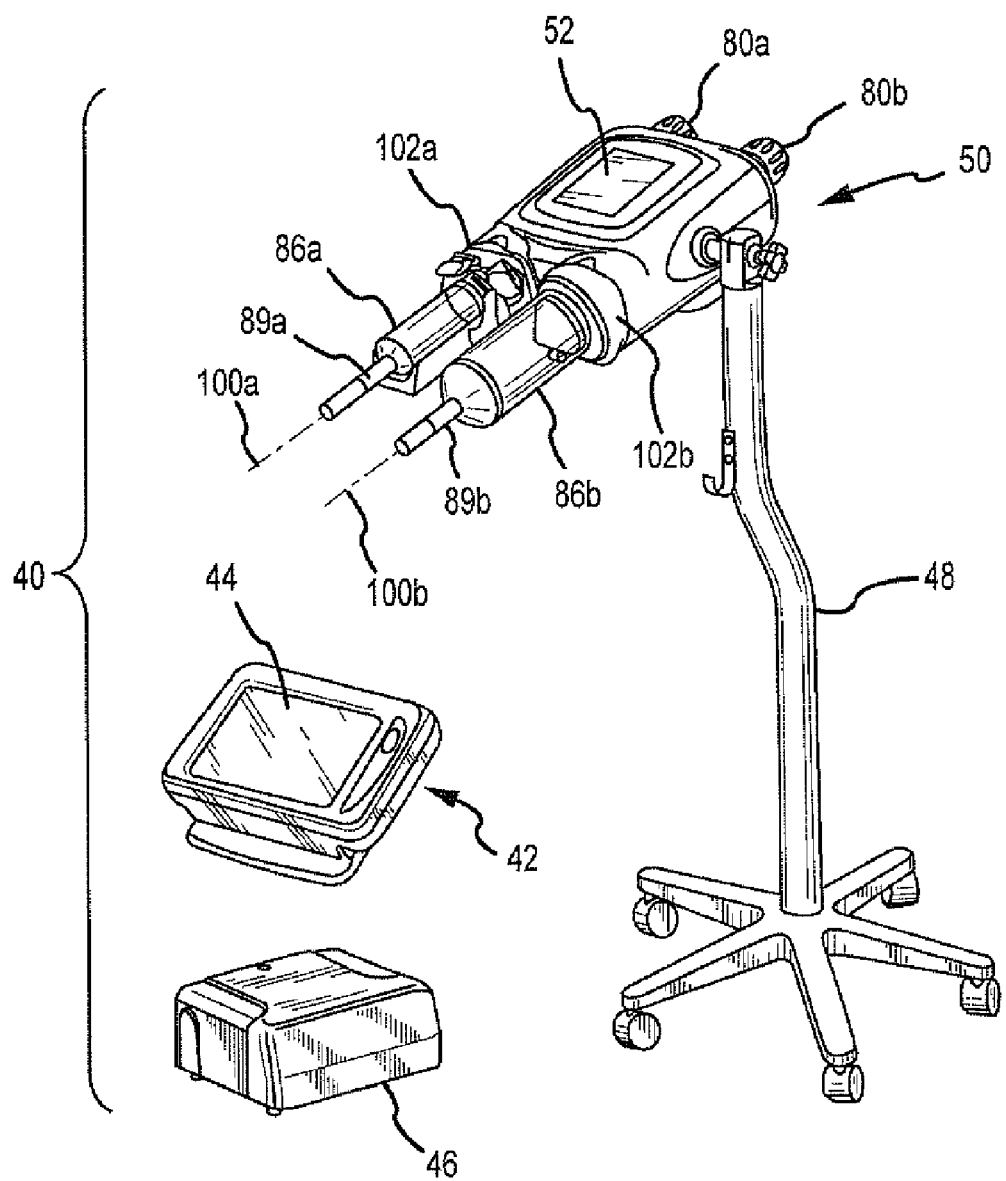
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 is mounted on the powerhead 50.

Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn could be mounted to an appropriate structure (e.g., ceiling, wall, floor). Any support assembly for the powerhead 50 may be positionally adjustable in at least some respect (e.g., by having one or more support sections that may be repositioned relative to one more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
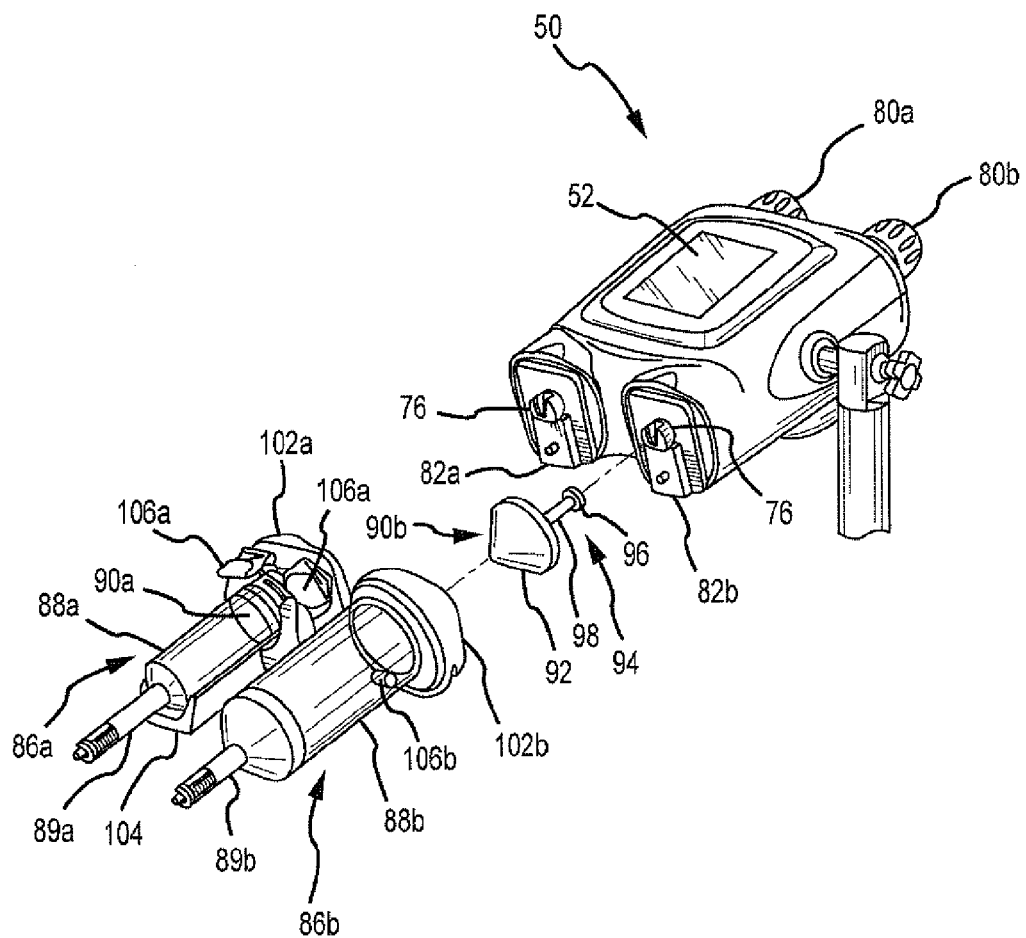
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within the syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74, which are each part of a syringe plunger drive assembly 56 for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74, which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
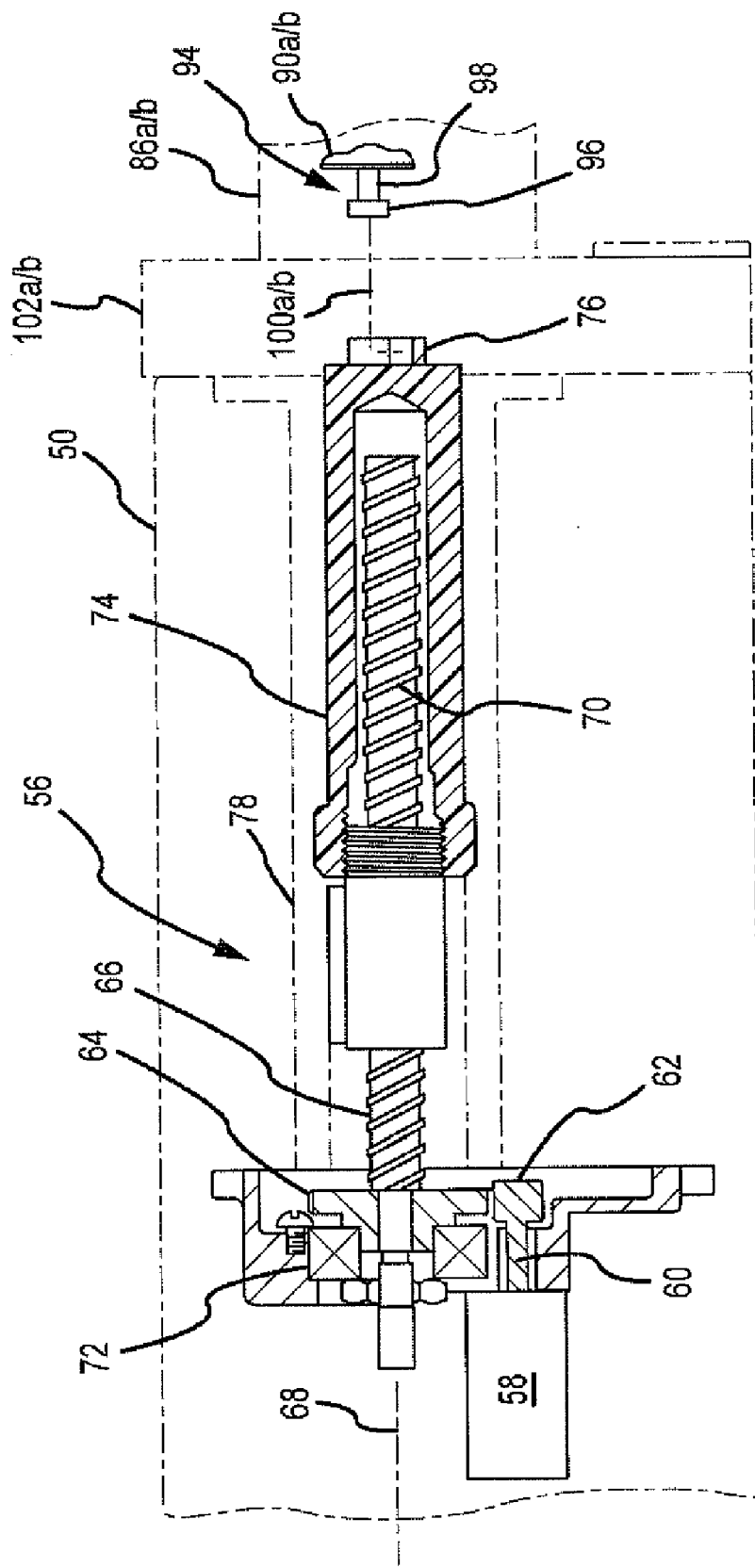
FIG. 2C is a schematic of one embodiment of a syringe plunger drive assembly used by the power injector of FIG. 2k

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, SPECT imaging, PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Each such syringe utilized by each of the power injectors 10, 40 may include any appropriate fluid, for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

It may be desirable to perform a patency check in preparation for using a power injector to inject fluid into a patient (e.g., to execute an injection protocol). Consider the case where the power injector is of the dual-head type discussed above in relation to FIGS. 2A-C (i.e., where the power injector 40 utilizes a pair of syringes 86a, 86b). The "A" side of this type of power injector may be for injecting contrast media (e.g., corresponding with syringe 86a), while the "B" side of this type of power injector may be for injecting saline (e.g., corresponding with syringe 86b). An initial saline injection (e.g., using only a portion of the saline in the syringe 86b, such that there is enough saline left in the syringe 86b to execute the injection protocol) may be characterized as a patency check injection. One type of patency check protocol will be discussed in relation to this type of power injector.

The power injector software may include one or more routines that assist an operator in selecting an optimum flow rate and volume for the saline injection test portion of a patency check. A patency check interface screen may suggest to the operator flow rate and/or volume values that are based on the selected injection protocol so as to provide a simulation that is substantially similar to the imaging injection that is to follow (e.g., in accordance with a selected injection protocol). This additional functionality may be included via a separate, dedicated display on the powerhead and/or console, or may be one of the many menu screens typically presented to an operator through a general interface screen. Also, the software may automatically set the flow rate and volume, or may permit the operator to set, or modify, the values after seeing the suggested values. Certain safeguards may be included such that a patency check injection may not be performed until an injection protocol has been enabled or until a manual purge has been completed. Also, the patency check injection may include a verification that enough saline remains available for the injection protocol, before proceeding with the patency check injection.

Figure 3:
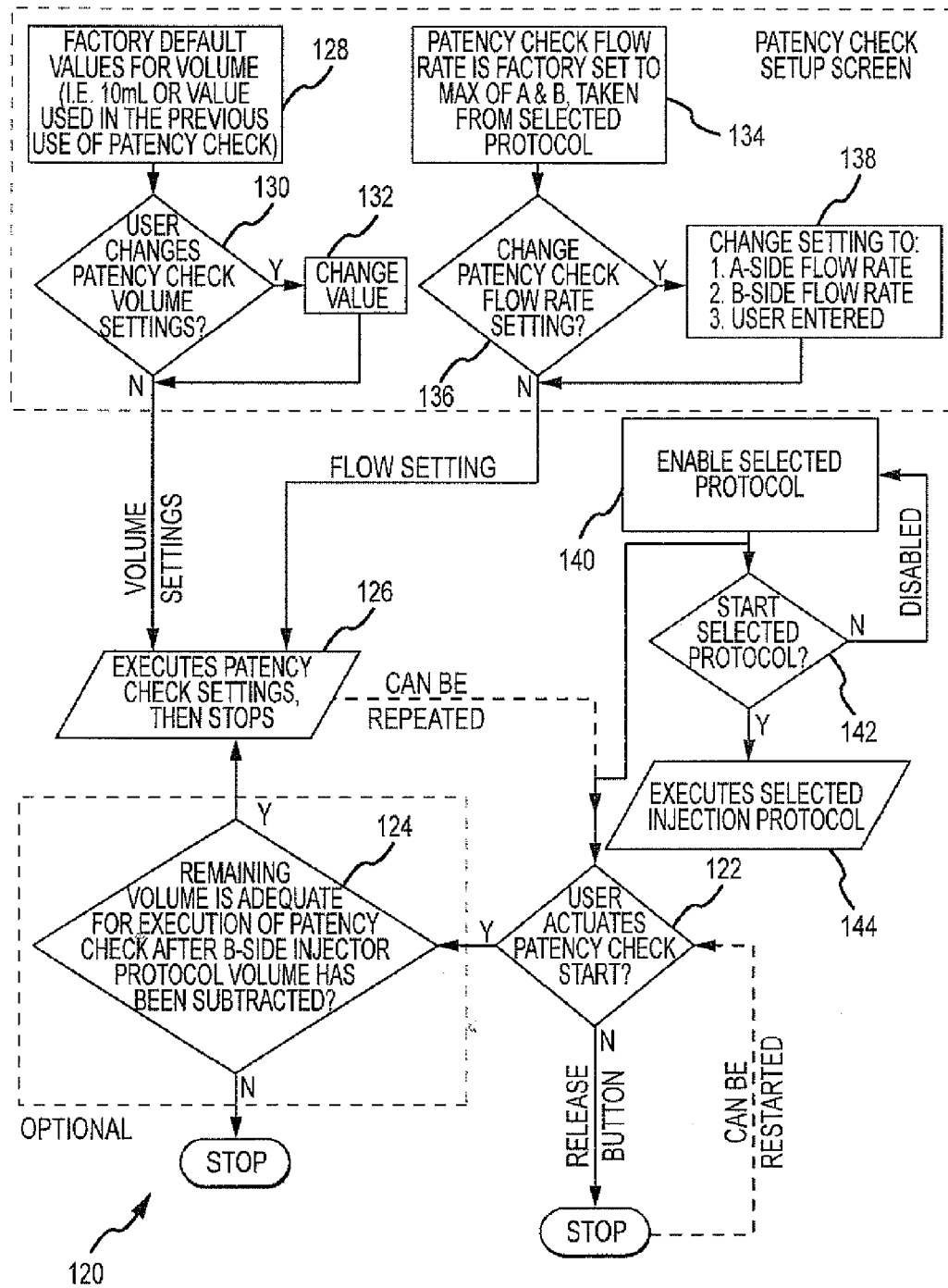
FIG. 3 is one embodiment of a patency check injection protocol.

In general, a patency check can be implemented according to an exemplary algorithm or protocol 120 that is depicted in the flowchart of FIG. 3. In step 140, an injection protocol is selected and enabled. Before the injection protocol is actually performed, however, the operator may want to perform a patency check, and activates the patency check (step 122). In an exemplary embodiment, the operator indicates a desire to perform a patency check by pressing and holding an expel button on the powerhead for the saline syringe for a given period of time, although numerous other interface methodologies may be used to permit the operator to initiate a patency check. As shown in the flowchart, the specific methodology discussed here requires that the operator press a button for more than a threshold time, thus ensuring that a patency check in not unintentionally initiated. If the button is released too early, no patency check is performed, but may be re-initiated as illustrated at step 122.

In the described embodiment, the power injector software performs an optional check in step 124 to determine if adequate fluid exists to perform the patency check and the selected injection protocol (i.e., the injection protocol may require one or more injections of both contrast media and saline). If there is not an adequate amount of saline in the syringe to do both a patency check injection and an injection in accordance with the selected protocol from step 140, the process stops. However, if there is a sufficient amount of saline in the syringe, then the patency check may be executed in step 126.

Based on the selected injection protocol, an operator may be presented interface options to set up the patency check. These options may derive from the existing injection protocol or from settings made by the operator. As seen at step 128, a volume for the patency check may be derived from a factory default, or a historical volume used from previous patency checks. As shown at step 130, the operator may be presented with the opportunity to change the volume if desired. If so, then the volume value is changed in step 132. As seen at step 134, a flow rate may also be selected for the patency check. Again, this could be based on the injection protocol, a default value, or historical data. In the described embodiment, the default flow rate is selected to be the maximum flow rate on the "A" or "B" sides of the power injector, so that the patency check verifies that lack of extravasation at the largest flow rate that will be required. Here again, the operator is provided the option of changing the patency check derivation in step 136—if desired the user may choose the "A" side flow rate or maximum "A" side flow rate, or the "B" side flow rate or maximum "B" side flow rate, in step 138.

Once the operator has been presented with patency check settings (e.g., in a setup screen displayed immediately after step 124), the operator may execute the patency check in step 126. Assuming no extravasation is evident, the operator would typically proceed to enable the injection protocol in step 140, at which point the power injector may await a "start" indication from the operator in step 142, upon which the injection protocol may be executed in step 144. If there is extravasation seen during the patency check, this may be remedied, and another patency check may be performed.

Figure 4:
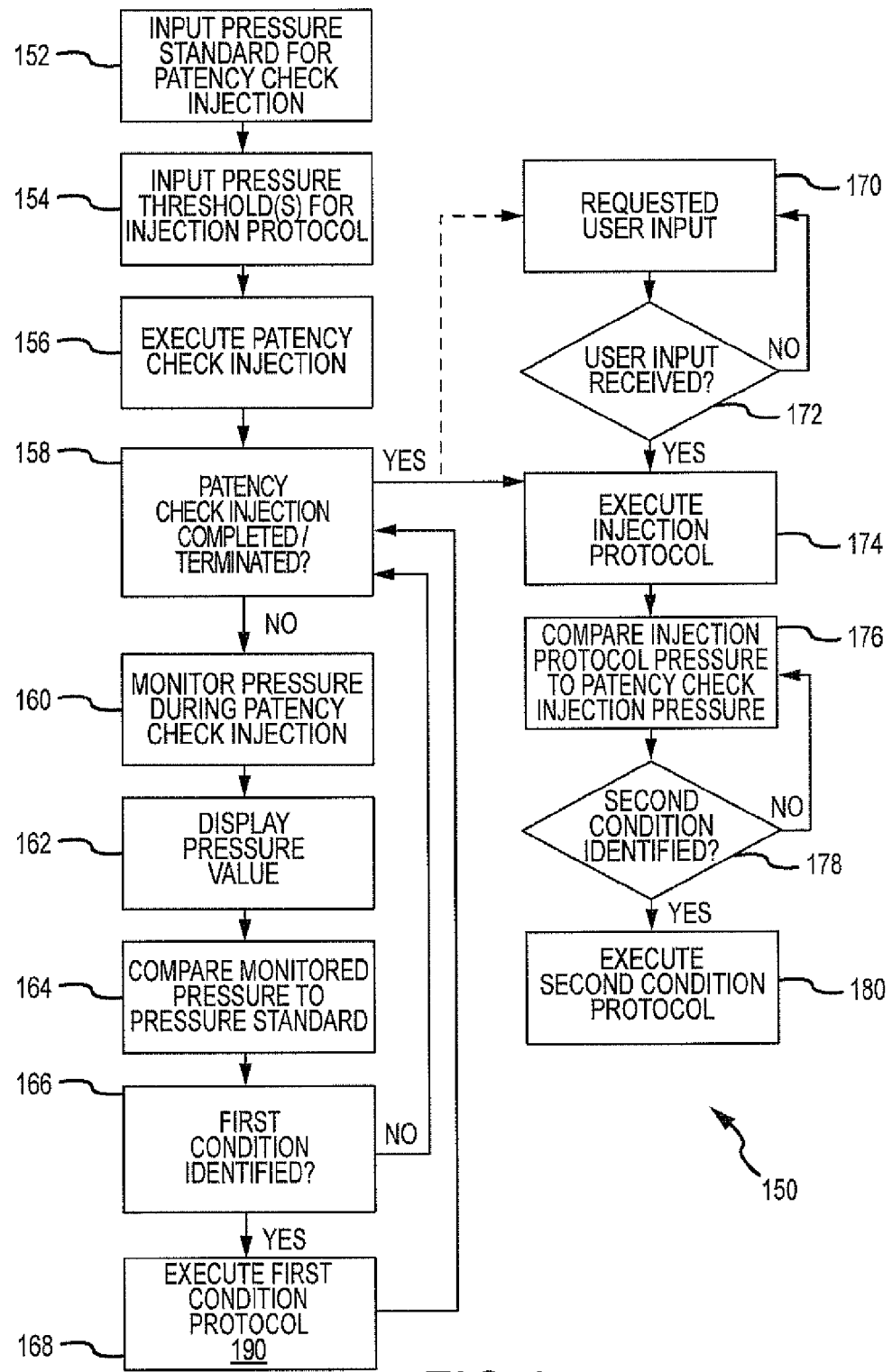
FIG. 4 is one embodiment of a patency check injection protocol that utilizes a stored pressure standard.

FIG. 4 illustrates one embodiment of a patency check that utilizes a stored pressure standard or the like. The patency check protocol 150 may be implemented or integrated in any appropriate manner (e.g., in the power injector software; implemented by software, hardware, firmware, and any combination thereof). In one embodiment, the patency check protocol 150 is executed by one or more processors of any appropriate size, shape, configuration and/or type. In one embodiment the patency check protocol 150 is executed using one or more computers.

Step 152 of the patency check protocol 150 allows for a pressure standard to be input. This pressure standard will be used in the assessment of the actual patency check injection. The patency check protocol 150 also allows one or more pressure thresholds to be input through execution of step 154, where each such pressure threshold is for an injection in accordance with an injection protocol that is to be executed after a patency check injection. The injection protocol is that which controls the actual injection (e.g., for imaging or therapeutic purposes). It should be appreciated that step 154 could be executed outside of the patency check protocol 150 as an alternative to the illustrated embodiment.

The pressure standard associated with step 152 of the patency check protocol 150 may be in any appropriate form, may be input or entered in any appropriate manner, may be input or entered at any appropriate time, may be input or entered at any appropriate location, and may be stored at any appropriate location and in any appropriate manner. The patency check protocol 150 may be configured to allow an operator to input, enter or otherwise select: 1) a pressure standard on each execution of the protocol 150; 2) to utilize a default pressure standard on each execution of the protocol 150; 3) to utilize the pressure standard from the most recentin-time execution of the patency check protocol 150; or 4) to retrieve a pressure standard stored in memory. In one embodiment, the pressure standard is in the form of a pressure limit or a pressure threshold (e.g., a single value, such as 200 psi). In another embodiment, the pressure standard is in the form of a target pressure curve or the like. This target pressure curve may be generated in any appropriate manner (e.g., empirically), and may represent the change in pressure over time during a patency check injection for the case where there is acceptable flowpath from the power injector to the patient (e.g., no substantial blockage in the flowpath), where there is an acceptable venous access (e.g., the flowpath from the power injector terminates within a vein versus tissue), or both.

A patency check injection may be initiated through execution of step 156 of the patency check protocol 150, for instance at least generally in accordance with the patency check protocol 120 of FIG. 3. In one embodiment, the patency check injection associated with step 156 entails injecting a small volume of saline (e.g., no more than about 20 milliliters) into the patient at the maximum flow rate that will be used by the injection protocol, and which many be executed after a patency check has been completed. In any case, the status of the patency check injection may be monitored through execution of step 158, and which may be executed in any appropriate manner.

The pressure or back-pressure in the flowpath from the power injector to the patient is monitored during the patency check injection through step 160 of the patency check protocol 150. This pressure or back-pressure may be monitored in any appropriate manner (e.g., by monitoring the motor current being used by the power inject to discharge fluid for the patency check injection, using a load cell, or using a pressure transducer). The pressure or back-pressure may also be displayed at any appropriate location and at any appropriate time through execution of step 162. For instance, a pressure or back-pressure associated with the patency check injection may be displayed on a powerhead display, on a remote console operatively interconnected with a powerhead, or both. The pressure or back-pressure may be displayed on a real-time basis. The maximum pressure or back-pressure that was identified during the patency check injection may be displayed at the completion of the patency check injection. A current value of the pressure or back-pressure may be displayed on a real-time basis, and the maximum pressure or back-pressure that was identified during the patency check may also be displayed after the patency check injection has been completed.

The monitored pressure from step 160 may be compared to the pressure standard of step 152 through execution of step 164 of the patency check protocol 150. This comparison may be undertaken in any appropriate manner and on any appropriate basis (e.g., using a computer). In one embodiment, step 164 provides for a real-time comparison of the pressure values from step 160 with the pressure standard of step 152. Step 164 provides a comparison between the pressure values of step 160 and the pressure standard of step 152 for purposes of identifying a first condition pursuant to step 166. This "first condition" may be defined in any appropriate manner. In one embodiment, a first condition in accordance with step 166 exists when the pressure from step 160 meets or exceeds the pressure standard of step 152 (e.g., when the pressure standard is in the form of a pressure limit or threshold). In another embodiment, a first condition in accordance with step 166 exists when the pressure from step 160 deviates from the pressure standard of 152 by more than a certain amount (e.g., when the pressure standard is in the form of a target pressure curve).

Figure 5:
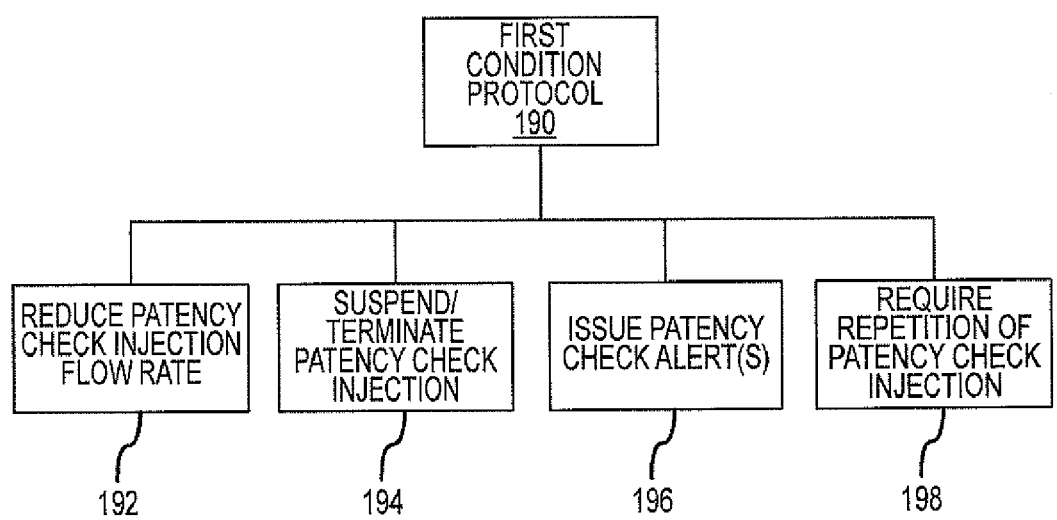
FIG. 5 is one embodiment of a protocol that may be executed when a first condition is identified by the patency check injection protocol of FIG. 4.

If the comparison of step 164 of the patency check protocol 150 identifies a first condition via step 166, the protocol 150 proceeds to step 168 where a first condition protocol 190 is executed. The first condition protocol 190 may execute any appropriate action or combination of actions in response to the patency check protocol 150 identifying the existence of a first condition. Representative actions for the first condition protocol 190 are illustrated in FIG. 5, and will be discussed in more detail below.

When the patency check injection has been completed or has been terminated, step 158 of the patency check protocol 150 may be configured to request user input pursuant to step 170. For instance, step 170 may request the operator to acknowledge that the injection protocol may be initiated, that the patency check may be cleared, or both. This request from step 170 may be presented in any appropriate manner and at any appropriate location, for instance on a display associated with the power injector (e.g., on the powerhead, on a remote console, or the like). The patency check protocol 150 may be configured to require this type of user input (through step 172) before allowing the selected injection protocol to be initiated or enabled. Once user input has been received through execution of step 172, and which may be input in any appropriate manner (e.g., "clicking" a button on a user interface screen, touching a button on a user interface screen), the patency check protocol 150 may proceed from step 172 to step 174, where the injection protocol may be initiated/executed in any appropriate manner.

Steps 170 and 172 of the patency check protocol 150 may not be required in each instance, or at least may not be required for at least certain instances. For instance, if the patency check injection was completed without a first condition being identified through execution of steps 160, 164 and 166, the patency check protocol 150 could be configured to automatically initiate execution of the injection protocol through execution of step 174 (e.g., steps 170 and 172 could be bypassed in this instance). However, steps 170 and 172 could be required even if the patency check injection was completed without a first condition being identified through execution of steps 160,164 and 166.

Step 168 or step 172 each could be considered as the end of the patency check protocol 150. However, the illustrated embodiment continues with a step 176 that is directed to comparing an injection protocol pressure with a patency check injection pressure. For instance, the pressure in the flowpath from the power injector to the patient may be monitored in any appropriate manner throughout execution of the selected injection protocol (e.g., pursuant to step 174), and may be compared with a pressure encountered during the patency check injection (e.g., the maximum pressure that was identified through execution of step 160; the average pressure that was identified through execution of step 160). If the comparison of step 176 of the patency check protocol 150 identifies a second condition via step 178, the protocol 150 proceeds to step 180, where a second condition protocol is executed. A "second condition" may be where the pressure value during the execution of the injection protocol exceeds a representative pressure value from the patency check injection by more than a certain amount. The second condition protocol may execute any appropriate action or combination of actions in response to the patency check protocol 150 identifying a second condition and pursuant to step 180, for instance at least generally of the type when the patency check protocol 150 identifies the existence of a first condition during the patency check injection.

Any appropriate action or combination of actions may be undertaken if the patency check protocol 150 of FIG. 4 identifies the existence of a first condition during a patency check injection. FIG. 5 illustrates various representative actions that could be undertaken. The flow rate being used for the patency check injection could be reduced in accordance with step 192 of the first condition protocol 190. The patency check injection could be suspended or terminated through execution of step 194 of the first condition protocol 190. For instance, this may allow an operator and/or technologist to investigate the situation (e.g., to determine if there is any obvious "kink" or the like in a tubing set extending from the power injector to the patient).

One or more patency check alerts or notifications could be issued in any appropriate manner if the patency check protocol 150 identifies a first condition. Each such alert or notification may be in any appropriate form, may be presented at any appropriate location through execution of step 196 of the first condition protocol 190 of FIG. 5, or both. Representative alerts include displaying an appropriate message (e.g., investigate potential blockage, investigate injection site, or both), activating one or more optical or visual indicators or alerts (e.g., the noted message or messages may flash, a pressure value may flash on a display), activating one or more audible indicators (e.g., an alarm), or the like. The first condition protocol 190 may also be configured to require that the patency check injection be repeated through execution of step 198.

Figure 6:
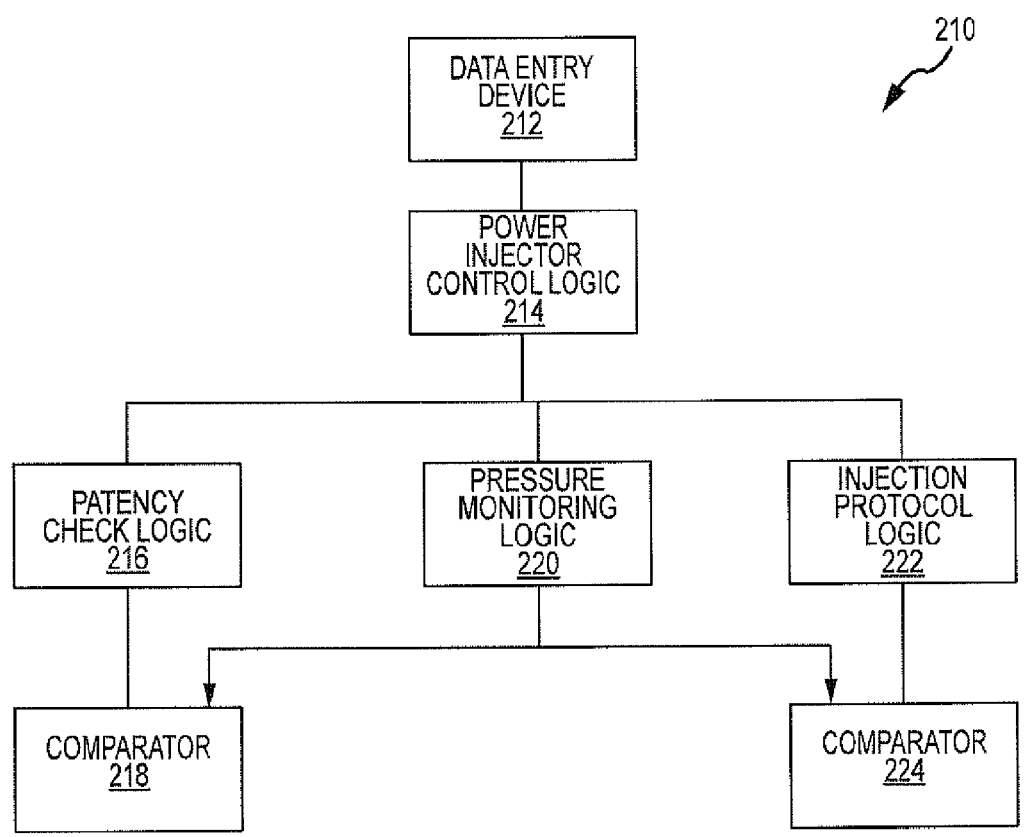
FIG. 6 is one embodiment of a power injector control system that may incorporate the patency check injection protocol of FIG. 4.

The patency check protocol 150 of FIG. 4 and the first condition protocol 190 of FIG. 5 each may be implemented in any appropriate manner (e.g., software, hardware, firmware, and any combination thereof). FIG. 6 illustrates one representative implementation in the form of a power injector control system 210. The power injector control system 210 includes one or more data entry devices 212 (e.g., a mouse, keyboard, a touch screen display, a soft key display, a touch pad, a track ball) that is operatively interconnected with what may be characterized as a power injector control module or logic 214. Three separate modules, logics, or functionalities are part of or utilized by the power injector control logic 214, and each may be implemented and/or executed in any appropriate manner (e.g., using one or more processors; using one or more computers). One is a patency check module or logic 216 that may be configured to execute the patency check protocol 150 of FIG. 4 and the first condition protocol 190 of FIG. 5. For instance, the patency check logic 216 may utilize a comparator 218 of any appropriate configuration and/or type for purposes of executing steps 164 and 166 of the patency check protocol 150.

The power injector control logic 214 also includes a pressure monitoring module or logic 220. This pressure monitoring logic 220 may control the pressure monitoring function associated with step 160 of the patency check protocol 150, may provide for the monitoring of pressure during the execution of an injection protocol, or both. Any way of monitoring pressure may be utilized by the pressure monitoring logic 220. Finally, the power injector control system 210 includes what may be characterized as an injection protocol module or logic 222. The injection protocol logic 222 may be configured to execute a desired injection protocol, and may utilize a comparator 224 of any appropriate configuration and/or type for purposes of executing steps 176 and 178 of the patency check protocol 150.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A power injector, comprising:
a powerhead;
a syringe plunger drive assembly;
patency check logic configured to execute a patency check injection to assess for both blockage in a flowpath to a patient's vein and existence of an extravasation condition where fluid is being introduced into a patient's tissue instead of a vein, wherein said patency check logic comprises a pressure standard;
pressure monitoring logic, wherein an output from said pressure monitoring logic is provided to said patency check logic for comparison with said pressure standard, wherein said patency check logic is configured to identify an existence of a first condition, wherein said first condition is either when a monitored pressure during a patency check injection reaches or exceeds a pressure threshold, or when a monitored pressure during a patency check injection deviates from a target pressure curve by more than a certain amount; and
injection protocol logic, separate from said patency check logic, configured to execute an injection protocol after said patency check logic executes a patency check injection, wherein said injection protocol logic comprises a comparator, wherein a first input to said comparator comprises a pressure from a patency check injection when said patency check logic failed to identify an occurrence of said first condition, and wherein a second input to said comparator comprises a monitored pressure during a subsequent execution of an injection protocol.

2. The power injector of claim 1, further comprising a syringe mounted on said powerhead, wherein said syringe comprises a syringe barrel and a plunger movably disposed within said syringe barrel, and wherein said syringe plunger drive assembly may interact with said plunger to move said plunger.

3. The power injector of claim 1, wherein said first input for said comparator is one of a maximum pressure encountered during a patency check injection and an average pressure encountered during a patency check injection.

4. The power injector of claim 1, wherein said pressure monitoring logic is configured to monitor a back-pressure during a patency check injection.

5. The power injector of claim 1, wherein said pressure standard comprises said pressure threshold.

6. The power injector of claim 1, wherein said pressure standard comprises said target pressure curve.

7. The power injector of claim 1, further comprising at least one data entry device operatively interconnected with said patency check logic, wherein said pressure standard may be input using said at least one data entry device.

8. The power injector of claim 7, wherein said at least one data entry device is selected from the group consisting of a touch screen display, a soft key display, a keyboard, a mouse, touch pad, and a track ball.

9. The power injector of claim 1, further comprising a display, wherein said patency check logic is configured to present on said display a representation of a monitored pressure from a patency check injection.

10. The power injector of claim 9, wherein said representation of a monitored pressure is selected from the group consisting of a numeric representation of a pressure value, a graphical representation of a pressure value, or a combination thereof.

11. The power injector of claim 9, wherein said patency check logic is configured to present said representation of a monitored pressure on said display on a real-time basis.

12. The power injector of claim 9, wherein said patency check logic is configured to present said representation of a monitored pressure on said display after completion of a patency check injection.

13. The power injector of claim 1, wherein said patency check logic is configured to provide at least one notification when said patency check logic identifies an occurrence of said first condition.

14. The power injector of claim 13, wherein said at least one notification is selected from the group consisting of a textual message, an alphanumeric message, at least one visual alarm, at least one audible alarm, or any combination thereof.

15. The power injector of claim 1, wherein said patency check logic is configured to terminate a patency check injection if said patency check logic identifies an occurrence of said first condition.

16. The power injector of claim 1, wherein user input is required if said patency check logic identifies an occurrence of said first condition.

17. The power injector of claim 1, wherein said patency check logic is configured to reduce a flow rate for a patency check injection if said patency check logic identifies an occurrence of said first condition.

18. The power injector of claim 1, wherein said patency check logic is configured to initiate a first action if there is a first relationship between said pressure standard and a monitored pressure from a patency check injection, wherein said first action is selected from the group consisting of suspending the patency check injection, terminating the patency check injection, reducing a flow rate for the patency check injection, providing at least one notification, or any combination thereof.

19. The power injector of claim 1, wherein said patency check logic is configured to display a message upon completion of a patency check injection procedure.

20. The power injector of claim 19, wherein said injection protocol logic is operatively interconnected with said patency check logic, and wherein user input is required after execution of a patency check injection using said patency check logic and prior to executing an injection protocol using said injection protocol logic.

21. A method for executing a first medical procedure, comprising the steps of:
fluidly interconnecting a patient with a power injector;
injecting a first fluid into said patient using said power injector, wherein said first fluid is an initial fluid injected into said patient by said power injector for said first medical procedure;
monitoring said injecting a first fluid step for an occurrence of a first condition, wherein said first condition is either when a pressure during said injecting a first fluid step reaches or exceeds a pressure threshold, or when a pressure during said injecting a first fluid step deviates from a target pressure curve by more than a certain amount;
assessing for both blockage in a flowpath to said patient and existence of an extravasation condition where fluid is being introduced into said patient's tissue instead of a vein, said assessing step comprising comparing an output of said monitoring step for said first fluid with a first standard, wherein said comparing step is executed by power injector control logic;
injecting a second fluid into said patient using said power injector, wherein said injecting a second fluid step is executed after said injecting a first fluid step; and
monitoring said injecting a second fluid step, comprising comparing a pressure from said injecting a second fluid step with a pressure from said injecting a first fluid step when said monitoring step for said first fluid failed to identify an occurrence of said first condition.

22. A power injector, comprising:
a powerhead;
a syringe plunger drive assembly;
patency check logic configured to execute a patency check injection to assess for both blockage in a flowpath to a patient's vein and existence of an extravasation condition where fluid is being introduced into a patient's tissue instead of a vein, wherein said patency check logic comprises a pressure standard;
injection protocol logic, separate from said patency check logic, configured to execute an injection protocol after said patency check logic executes a patency check injection; and
pressure monitoring logic, wherein an output from said pressure monitoring logic is used by both said patency check logic and said injection protocol logic.

* * * * *